(12) United States Patent
Yamada

(10) Patent No.: US 12,291,703 B2
(45) Date of Patent: May 6, 2025

(54) GAS CONCENTRATION ADJUSTING AGENT FOR USE IN CULTURE OF BACTERIA, AND METHOD FOR CULTURING BACTERIUM USING SAME

(71) Applicant: MITSUBISHI GAS CHEMICAL COMPANY, INC., Tokyo (JP)

(72) Inventor: Hajime Yamada, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 385 days.

(21) Appl. No.: 17/439,080

(22) PCT Filed: Feb. 20, 2020

(86) PCT No.: PCT/JP2020/006689
§ 371 (c)(1),
(2) Date: Sep. 14, 2021

(87) PCT Pub. No.: WO2020/189167
PCT Pub. Date: Sep. 24, 2020

(65) Prior Publication Data
US 2022/0154130 A1  May 19, 2022

(30) Foreign Application Priority Data

Mar. 20, 2019 (JP) .................................. 2019-053078

(51) Int. Cl.
C12M 1/34 (2006.01)
C12N 1/20 (2006.01)

(52) U.S. Cl.
CPC .............. *C12M 41/34* (2013.01); *C12N 1/20* (2013.01)

(58) Field of Classification Search
CPC ....... C12M 41/34; C12N 1/20; B01J 37/0203; C01P 2006/14; C01P 2006/16
See application file for complete search history.

(56) References Cited

U.S. PATENT DOCUMENTS

| | | | |
|---|---|---|---|
| 5,914,070 A | 6/1999 | Araki et al. | |
| 6,114,162 A | 9/2000 | Kashiba | |
| 9,085,752 B2 * | 7/2015 | Oura | C12M 41/34 |
| 2006/0163534 A1 | 7/2006 | Sugimoto et al. | |
| 2012/0282690 A1 | 11/2012 | Oura et al. | |
| 2017/0209848 A1 | 7/2017 | Takenaka et al. | |

FOREIGN PATENT DOCUMENTS

| | | | |
|---|---|---|---|
| CN | 104783293 A | 7/2015 | |
| EP | 0 111 583 A1 | 6/1982 | |
| EP | 1 550 506 A1 | 7/2005 | |
| JP | 10-327845 A | 12/1998 | |
| JP | 3818324 B2 | 9/2006 | |
| JP | 5682831 B2 | 3/2015 | |
| KR | 10-2016-0134376 A | 11/2016 | |
| WO | 2011/065363 A1 | 6/2011 | |
| WO | WO-2019131207 A1 * | 7/2019 | .............. B01J 20/20 |

OTHER PUBLICATIONS

Kumar, A. and Jena, H.M. (2016) Preparation and Characterization of High Surface Area Activated Carbon from Fox Nut (*Euryale ferox*) Shell by Chemical Activation with H3PO4. Results in Physics, 6, 651-658. (Year: 2016).*
Ilomuanya MO, Nashiru B, Ifudu ND, Igwilo CI. Effect of pore size and morphology of activated charcoal prepared from midribs of Elaeis guineensis on adsorption of poisons using metronidazole and *Escherichia coli* O157:H7 as a case study. J Microsc Ultrastruct. Jan.-Mar. 2017;5(1):32-38 (Year: 2017).*
Wang, X., Li, D., Li, W., Peng, J., Xia, H., Zhang, L., Guo, S., and Chen, G. (2013). "Optimization of mesoporous activated carbon from coconut shells by chemical activation with phosphoric acid," BioRes. 8(4), 6184-6195. (Year: 2013).*
Khalil et al.(Adsorption Science & Technology vol. 18 No. 4 2000; p. 373-383) (Year: 2000).*
International Search Report issued in International Patent Application No. PCT/JP2020/006689, dated Apr. 21, 2020, along with English translation thereof.
Written Opinion of the International Searching Authority issued in International Patent Application No. PCT/JP2020/006689, dated Apr. 21, 2020, along with English translation thereof.
Office Action issued in Chinese Patent Application No. 202080020317.5, Dec. 21, 2023, translation.

* cited by examiner

*Primary Examiner* — Thomas J. Visone
*Assistant Examiner* — Georgiana C Reglas
(74) *Attorney, Agent, or Firm* — GREENBLUM & BERNSTEIN P.L.C.

(57) ABSTRACT

A gas concentration regulator for use in culture of bacteria, including: (a) an ascorbic acid component; (b) a transition metal catalyst; (c) activated carbon; (d) an alkali metal carbonate or an alkaline earth metal hydroxide; and (e) water, wherein the activated carbon is impregnated with the ascorbic acid component and the water, and an average pore diameter of the activated carbon is 2.0 nm or more.

5 Claims, No Drawings

GAS CONCENTRATION ADJUSTING AGENT FOR USE IN CULTURE OF BACTERIA, AND METHOD FOR CULTURING BACTERIUM USING SAME

TECHNICAL FIELD

The present invention relates to a gas concentration regulator for use in culture of bacteria and a method for culturing bacteria using the same.

BACKGROUND ART

In culture of biological samples such as tissues or cells performed in research fields or industrial fields of biology, reproduction, or biotechnology, a gas environment that differs from the atmosphere is required. For example, it is necessary to set an atmospheric carbon dioxide concentration to about 5% as a condition to keep the pH of a bicarbonate buffer-based culture solution at pH 7.4, which is the same as pH of blood in the normal state. Further, in many research fields, culture of cells in a low-concentration oxygen atmosphere similar to that in vivo has been performed.

As a means for producing a gas environment with a high-concentration carbon dioxide atmosphere and a low-concentration oxygen atmosphere, a carbon dioxide gas incubator is known; however, there is issue that burden such as equipment costs and management of high-pressure gases is large. Accordingly, in recent years, there has been widely used a method in which a gas concentration regulator utilizing an oxidation reaction of an ascorbic acid component is used (see Patent Documents 1 and 2).

CITATION LIST

Patent Documents

Patent Document 1: JP 3818324 B
Patent Document 2: JP 5682831 B

SUMMARY OF INVENTION

Technical Problem

In culture of bacteria, it is required to produce a gas environment with a high-concentration carbon dioxide atmosphere and a low-concentration oxygen atmosphere for the shortest possible time.

Thus, the problem to be solved by the present invention is to provide a gas concentration regulator for use in culture of bacteria that generates a large amount of carbon dioxide in the reaction initial stage (1 hour after reaction initiation) of the oxidation reaction of an ascorbic acid component.

Solution to Problem

As a result of diligent research, the present inventor has found that an average pore diameter of activated carbon, which is a carrier for the gas concentration regulator, affects the amount of carbon dioxide generated in the reaction initial stage of the oxidation reaction of an ascorbic acid component. The present invention has been completed based on such finding.

That is, the present invention relates to the following.

<1> A gas concentration regulator for use in culture of bacteria, including: (a) an ascorbic acid component; (b) a transition metal catalyst; (c) activated carbon; (d) an alkali metal carbonate or an alkaline earth metal hydroxide; and (e) water, wherein the activated carbon is impregnated with the ascorbic acid component and the water, and an average pore diameter of the activated carbon is 2.0 nm or more.

<2> The gas concentration regulator according to <1> above, wherein the average pore diameter of the activated carbon is 2.0 nm or more and 5.5 nm or less.

<3> The gas concentration regulator according to <1> or <2> above, wherein a total pore volume of the activated carbon is 0.60 $cm^3/g$ or more.

<4> Use of the gas concentration regulator according to any one of <1> to <3> above in culture of bacteria.

<5> A method of culturing bacteria, including culturing bacteria in the presence of the gas concentration regulator according to any one of <1> to <3> above.

<6> A gas concentration regulator package, in which the gas concentration regulator according to any one of <1> to <3> above is bagged in an individual bag using an air-permeable packaging material.

Advantageous Effects of Invention

The gas concentration regulator for use in culture of bacteria according to the present invention generates a large amount of carbon dioxide in the reaction initial stage (1 hour after reaction initiation) of the oxidation reaction of an ascorbic acid component, so that it is possible to produce a gas environment with a high-concentration carbon dioxide atmosphere and a low-concentration oxygen atmosphere in a short period of time. If a gas concentration is set to a predetermined level as described later, the gas concentration regulator can be used for culture of any of anaerobic bacteria, microaerophilic bacteria, and aerobic bacteria.

DESCRIPTION OF EMBODIMENTS

An embodiment according to the present invention will be described below. The content of the present invention is not limited to the embodiment described below.

Note that in the present specification, a phrase of "A to B" indicating a numerical range means "more than or equal to A and less than or equal to B" (in the case of A<B), or "less than or equal to A and more than or equal to B" (in the case of A>B). Furthermore, in the present invention, a combination of preferable aspects is a more preferable aspect.

[Gas Concentration Regulator]

A gas concentration regulator for use in culture of bacteria according to the present invention is a gas concentration regulator including: (a) an ascorbic acid component; (b) a transition metal catalyst; (c) activated carbon; (d) an alkali metal carbonate or an alkaline earth metal hydroxide; and (e) water, in which the activated carbon is impregnated with the ascorbic acid component and the water, and an average pore diameter of the activated carbon is 2.0 nm or more. The gas concentration regulator is preferably used as a package in which a composition including (a) an ascorbic acid component, (b) a transition metal catalyst, (c) activated carbon, (d) an alkali metal carbonate or an alkaline earth metal hydroxide, and (e) water is packaged using an air-permeable packaging material. The gas concentration regulator according to the present invention is used in culture of bacteria.

(a) Ascorbic Acid Component

The gas concentration regulator according to the present invention includes an ascorbic acid component having both an oxygen absorption capacity and a carbon dioxide gas generation capacity as a main agent of an oxygen absorption reaction.

The ascorbic acid component means L-ascorbic acid and stereoisomers thereof, as well as salts and hydrates thereof. Examples of L-ascorbic acid salts include sodium L-ascorbate, potassium L-ascorbate, calcium L-ascorbate, and the like. Examples of stereoisomers of L-ascorbic acid include erythorbic acid (D-isoascorbic acid) and the like. Examples of erythorbic acid salts include sodium erythorbate, potassium erythorbate, calcium erythorbate, and the like. One ascorbic acid component may be used alone, or two or more may be used in combination.

In the gas concentration regulator according to the present invention, activated carbon is impregnated with the ascorbic acid component and water from the viewpoint of oxygen absorption performance. Specifically, activated carbon, which is a porous carrier, is impregnated with an aqueous solution of the ascorbic acid component in which the ascorbic acid component is dissolved in water. At this time, when the concentration of the ascorbic acid component in the aqueous solution is higher, the usage amount of the porous carrier can be reduced, and thus it is preferable to make the concentration of the ascorbic acid component at a concentration as close as possible to the saturation solubility. Due to this, it is preferable to select, as the ascorbic acid component, a compound having a high solubility in water, and specifically, sodium L-ascorbate is preferable. When sodium L-ascorbate is used, the concentration in the aqueous solution is suitably set to from 40 to 55 mass %.

In the gas concentration regulator, the oxidation reaction of the ascorbic acid component is utilized to absorb oxygen in the atmosphere, thereby adjusting the concentration thereof, and carbon dioxide generated by the oxidation reaction is utilized to adjust the carbon dioxide concentration in the atmosphere. Note that in the oxidation reaction, carbon dioxide is theoretically generated in a molar amount equivalent to that of oxygen molecules consumed. In accordance with the principle described above, when the oxygen concentration is reduced, the carbon dioxide concentration also increases in connection with this. However, when a compound having a carbon dioxide absorption capacity, for example, an alkaline earth metal hydroxide, is compounded in the gas concentration regulator, it is possible to suppress increase in carbon dioxide. Conversely, in a case where a compound having a carbon dioxide generating capability is compounded in the gas concentration regulator, it is possible to generate carbon dioxide in an amount equal to or more than a decreased amount of oxygen. In this way, in the gas concentration regulator according to the present invention, when the compounded components and/or the compounded amount of the composition constituting the gas concentration regulator are appropriately selected, and an extent of the oxidation reaction and an amount of carbon dioxide generated are adjusted, it is possible to adjust a specific atmosphere to desired oxygen concentration and carbon dioxide concentration. By adjusting the specific environment to the desired oxygen concentration and carbon dioxide concentration, it is possible to adjust a suitable culture environment for each of anaerobic bacteria, microaerophilic bacteria, or aerobic bacteria.

(b) Transition Metal Catalyst

The gas concentration regulator according to the present invention includes a transition metal catalyst that promotes progression of the oxidation reaction of the ascorbic acid component.

The transition metal catalyst is a catalyst having a metal compound such as a salt or an oxide of transition metal. Examples of suitable transition metal include iron, manganese, zinc, copper, and cobalt. Examples of the salt of transition metal include halides and mineral acid salts of transition metal, for example, chlorides and sulfates of transition metal. Representative examples thereof include anhydrates or hydrates of ferrous chloride, ferric chloride, ferrous sulfate, ferric sulfate, manganese chloride, zinc sulfate, copper sulfate, copper chloride, and cobalt sulfate, and among these, ferrous sulphate heptahydrate with good solubility in water and good compounding property is preferable.

From the viewpoint of promoting progression of the oxidation reaction of the ascorbic acid component, the content of the transition metal catalyst in the gas concentration regulator is preferably 5 to 25 parts by mass and more preferably 10 to 20 parts by mass per 100 parts by mass of the ascorbic acid component.

(c) Activated Carbon

The gas concentration regulator according to the present invention includes activated carbon. The activated carbon functions as a carrier of being impregnated with the aqueous solution of the ascorbic acid component, and has a function of promoting progression of the oxidation reaction because the activated carbon has a large contact area with air due to its large specific surface area.

As the activated carbon, there can be used what is produced using sawdust, coal, a palm shell, or the like as a raw material by various production methods such as water vapor activation or agent activation using zinc chloride or the like. Furthermore, the activated carbon is used to support an aqueous solution or the like of the ascorbic acid component and filled in an individual bag in a granular form, and thus granular activated carbon is preferable. The particle diameter of the granular activated carbon is preferably 0.1 to 2 mm, and more preferably 0.5 to 1 mm, from the viewpoint of oxygen absorption performance and a filling property (flowability) into a package.

In the present invention, the average pore diameter of the activated carbon is 2.0 nm or more. When the average pore diameter of the activated carbon is 2.0 nm or more, the gas concentration regulator for use in culture of bacteria according to the present invention generates a large amount of carbon dioxide in the reaction initial stage (1 hour after reaction initiation) of the oxidation reaction of the ascorbic acid component, so that it is possible to produce a gas environment with a high-concentration carbon dioxide atmosphere and a low-concentration oxygen atmosphere in a short period of time. The average pore diameter of the activated carbon is preferably 2.2 nm or more, and more preferably 2.5 nm or more, from the viewpoint of the amount of carbon dioxide generated in the reaction initial stage (1 hour after reaction initiation) of the oxidation reaction of the ascorbic acid component. The upper limit of the average pore diameter of the activated carbon may be 5.5 nm or less, may be 5.0 nm or less, may be 4.5 nm or less, and may be 4.0 nm or less. Note that the average pore diameter of the activated carbon in the present invention is measured by a method described in Examples below.

Furthermore, in the present invention, the total pore volume of the activated carbon is preferably 0.60 $cm^3/g$ or more, more preferably 0.65 $cm^3/g$ or more, and even more preferably 0.68 $cm^3/g$ or more, from the viewpoint of the amount of carbon dioxide generated in the reaction initial stage (1 hour after reaction initiation) of the oxidation reaction of the ascorbic acid component. The upper limit of the total pore volume of the activated carbon may be 2.0 $cm^3/g$ or less, 1.8 $cm^3/g$ or less. 1.5 $cm^3/g$ or less, or 1.0 $cm^3/g$ or less. Note that the total pore volume of the activated carbon in the present invention is measured by a method described in Examples below.

The content of the activated carbon in the gas concentration regulator is preferably 50 to 400 parts by mass and more preferably 75 to 300 parts by mass per 100 parts by mass of the ascorbic acid component, from the viewpoint of the oxygen absorption performance and the filling property into the package.

(d) Alkali Metal Carbonate or Alkaline Earth Metal Hydroxide

The gas concentration regulator according to the present invention includes an alkali metal carbonate or an alkaline earth metal hydroxide to adjust the carbon dioxide concentration. The alkali metal carbonate is used to cause the oxidation reaction of the ascorbic acid component to rapidly proceed and to control a reaction field to an alkaline region. On the other hand, the alkaline earth metal hydroxide is used as a carbon dioxide gas absorber. Note that when the alkali metal carbonate and the alkaline earth metal hydroxide are used in combination, it is difficult to adjust the carbon dioxide concentration, and thus, it is not preferable to use both of them in combination.

As the alkali metal carbonate, a water-soluble alkali metal carbonate such as sodium carbonate, sodium hydrogen carbonate, or sodium carbonate hydrate is suitably used, and among them, sodium carbonate is particularly preferable.

As the alkaline earth metal hydroxide, calcium hydroxide, magnesium hydroxide, or mixtures thereof are particularly suitably used. When it is desired to absorb a large amount of carbon dioxide in a short period of time, an alkaline earth metal hydroxide having a high solubility in water and a high carbon dioxide absorption rate, such as calcium hydroxide, is suitably used. Furthermore, the amount of carbon dioxide generated is not always constant and changes from time to time. For example, in more rapidly forming a gas atmosphere with an oxygen concentration of 0% and a carbon dioxide concentration of 5%, all the oxygen in the atmosphere is absorbed at a time, so that a large amount of carbon dioxide is generated at a time immediately after the oxidation reaction of the ascorbic acid component begins, and then the amount of carbon dioxide generated rapidly decreases. In such a case, it is preferable to mix calcium hydroxide having a high carbon dioxide absorption rate and magnesium hydroxide having a slow carbon dioxide absorption rate.

The alkaline earth metal hydroxide is preferably powder, and the average particle diameter thereof is preferably from 1 to 100 μm, and more preferably from 2 to 50 μm.

The content of the alkali metal carbonate or the alkaline earth metal hydroxide in the gas concentration regulator is preferably from 10 to 200 parts by mass, more preferably from 15 to 150 parts by mass, and even more preferably from 20 to 100 parts by mass, per 100 parts by mass of the ascorbic acid component, from the viewpoint of the carbon dioxide concentration adjustment.

(e) Water

The gas concentration regulator according to the present invention includes water necessary for the oxidation reaction of the ascorbic acid component to proceed.

It is preferable to adopt an aspect in which the activated carbon is impregnated with the activated carbon water, from the viewpoint of obtaining the gas concentration regulator as a solid with fluidity. In the gas concentration regulator according to the present invention, the activated carbon is impregnated with water and the ascorbic acid component from the viewpoint of oxygen absorption performance. Specifically, the activated carbon, which is a porous carrier, is impregnated with an aqueous solution of the ascorbic acid component in which the ascorbic acid component is dissolved in water. Furthermore, soluble components other than the ascorbic acid component may be dissolved in water, or insoluble components may be dispersed in water.

The content of water in the gas concentration regulator is preferably from 100 to 200 parts by mass, more preferably from 110 to 180 parts by mass, and even more preferably from 120 to 180 parts by mass, per 100 parts by mass of the ascorbic acid component, from the viewpoint of causing the oxidation reaction of the ascorbic acid component to proceed.

(f) Additional Component

The gas concentration regulator according to the present invention may include components other than the above-mentioned components (a) to (e) as needed within a range that does not inhibit the effects of the present invention.

(f1) Thermoplastic Resin

The gas concentration regulator according to the present invention may include a thermoplastic resin to suppress excessive heat generation associated with the progression of an oxygen absorption reaction (oxidation reaction of the ascorbic acid component). The type of the thermoplastic resin is not particularly limited, but for example, polyethylene, polypropylene, ethylene-vinyl acetate copolymer, elastomer, or a mixture thereof can be used, and in particular, low molecular weight polyethylene, polypropylene, or a mixture thereof having a molecular weight of 10000 or less is suitably used from the viewpoint of ease of adjusting a softening point and a low odor impact.

From the viewpoint of miscibility with other components, the thermoplastic resin is preferably a granular body with a particle diameter from 1 to 500 μm, and more preferably a granular body with a particle diameter from 10 to 300 μm. In addition, from the viewpoint of more effectively suppressing heat generation, the softening point of the thermoplastic resin is preferably 90 to 125° C.

The content of the thermoplastic resin in the gas concentration regulator is preferably from 35 to 300 parts by mass and more preferably from 60 to 200 parts by mass per 100 parts by mass of the ascorbic acid component from the viewpoint of promoting the oxidation reaction of the ascorbic acid component.

(f2) Aldehyde Removal Agent

The gas concentration regulator according to the present invention may include an aldehyde removal agent to remove aldehyde that is predominately generated as a by-product with the progression of the oxidation reaction of the ascorbic acid component. As a compound having an aldehyde removal capability, various compounds such as amines are known, but ethylene urea, urea, arginine, lysine hydrochloride, or polyallylamine, each of which has a sufficient aldehyde removal capability, does not generate an irritating odor, and exhibits a high effect in a small amount, is preferably compounded, and ethylene urea exhibiting a high effect in a smaller amount is more preferable.

The aldehyde referred to herein means a compound having one or more formyl groups in its molecule, that is, aldehydes. In the present invention, the aldehyde typically means aldehyde that is generated as a by-product in the course of oxygen absorption or culture of bacteria, and includes any aldehyde as long as it is classified in the chemical field into aldehydes and it adversely affects the culture of bacteria. Specific examples thereof include formaldehyde and acetaldehyde.

The content of the aldehyde removal agent in the gas concentration regulator is preferably from 0.5 to 25 parts by mass, more preferably from 1.0 to 10 parts by mass, and even more preferably from 1.0 to 5.0 parts by mass per 100 parts by mass of the ascorbic acid component from the viewpoint of efficiently and economically removing aldehyde.

A method for producing a gas concentration regulator according to the present invention is not particularly limited, but examples thereof include a method in which a transition metal catalyst, an alkali metal carbonate or an alkaline earth metal hydroxide, and the like is dissolved in an aqueous solution of an ascorbic acid component and the solution is mixed with activated carbon so that the activated carbon is impregnated with the solution.

[Gas Concentration Regulator Package]

The gas concentration regulator can be made into a gas concentration regulator package by packaging the composition containing the components described above by a packaging material using an air-permeable packaging material in whole or in part.

(Packaging Material)

Examples of the packaging material include a packaging material having a bag shape formed by bonding two sheets of an air-permeable packaging material to each other, a packaging material having a bag shape formed by bonding one sheet of an air-permeable packaging material and one sheet of a non-air-permeable packaging material to each other, and a packaging material having a bag shape formed by folding one sheet of an air-permeable packaging material and sealing edges other than the folded portion.

Here, when the air-permeable packaging material and the non-air-permeable packaging material each have a quadrilateral shape, examples of the packaging material include a packaging material having a bag shape formed by overlapping two sheets of an air-permeable packaging material and heat-sealing their four sides, a packaging material having a bag shape formed by overlapping one sheet of an air-permeable packaging material and one sheet of a non-air-permeable packaging material and heat-sealing their four sides, and a packaging material having a bag shape formed by folding one sheet of an air-permeable packaging material and heat-sealing its three sides other than the folded portion. Furthermore, the packaging material may be a packaging material having a bag shape formed by forming an air-permeable packaging material into a tubular shape and heat-sealing both ends and the trunk portion of the resulting tubular body.

(Air-Permeable Packaging Material)

As the air-permeable packaging material, a packaging material through which oxygen and carbon dioxide pass is selected. Of these, a packaging material having an air permeability resistance of 600 seconds or less, more preferably 90 seconds or less by a Gurley tester method is suitably used. Here, the air permeability resistance refers to a value measured by a method in accordance with JIS P 8117 (1998). More specifically, it refers to a time period required for 100 mL of air to pass through an air-permeable packaging material using a Gurley densometer available from Toyo Seiki Seisaku-sho, Ltd.

As the air-permeable packaging material, in addition to paper or nonwoven fabric, which is obtained by imparting air permeability to a plastic film is used. As the plastic film, there can be used, for example, a laminate film obtained by laminating and bonding a film of polyethylene terephthalate, polyamide, polypropylene, polycarbonate, or the like, and a film of polyethylene, an ionomer, polybutadiene, ethylene acrylic acid copolymer, ethylene methacrylic acid copolymer, ethylene vinyl acetate copolymer, or the like as a sealing layer. These laminates can also be used as the air-permeable packaging material.

As the method of imparting air permeability, various methods can be employed, in addition to punching with a cold needle or a heat needle. When air permeability is imparted by punching, the air permeability can be freely adjusted by a diameter, the number, a material, and the like of holes to be punched.

The thickness of the laminated film is preferably from 50 to 300 μm, and particularly preferably from 60 to 250 μm. In this case, as compared to a case where the thickness deviates from the aforementioned range, the packaging material can be a packaging material that retains strength and has an excellent heat sealing property and packaging suitability.

In order to maintain the function for a long period of time, the gas concentration regulator package described above is preferably stored in a gas barrier container or bag before use, and taken from the gas barrier container or bag for use. In addition, when the gas concentration regulator package is used for utilization in culture of bacteria, it is preferable to perform sterilization using gamma radiation or the like on the package in advance.

[Method for Culturing Bacteria]

A method for culturing bacteria according to the present invention is a method for culturing bacteria in the presence of the gas concentration regulator. Specifically, the gas concentration regulator (preferably the gas concentration regulator package) is placed in a gas-barrier sealed container along with a culture vessel containing bacteria and a medium, and then sealed, and the sealed container is allowed to stand at a suitable temperature for culture of bacteria. At this time, for the purpose of measuring an amount of aldehyde generated in the gas-barrier sealed container, adjusting a humidity in the container, or the like, an open container containing distilled water may be placed in the sealed container. As the open container, in addition to the culture vessel, a beaker, a flask, and the like can be exemplified, and a container of the same type as the culture vessel containing the bacteria and the medium is preferable.

The oxygen concentration in the sealed container is preferably 6 to 14 volume % when culturing microaerophilic bacteria, and preferably 1 volume % or less when culturing anaerobic bacteria.

The carbon dioxide concentration in the sealed container is preferably from 1 to 10 volume %, more preferably from 2 to 10 volume %, and even more preferably from 2 to 9 volume % when culturing microaerophilic bacteria. When anaerobic bacteria are cultured, the carbon dioxide concentration is preferably 10 volume % or more, more preferably 12 volume % or more, and even more preferably 14 volume % or more.

Although appropriate oxygen and carbon dioxide concentrations are different depending on bacteria, it is important to make a desired concentration in a short period of time. When microaerophilic bacteria are cultured, the oxygen concentration in the reaction initial stage (1 hour after reaction initiation) of the oxidation reaction of the ascorbic acid component is preferably from 2 to 18 volume %, more preferably from 3 to 17 volume %, and even more preferably from 4 to 16 volume %. The carbon dioxide concentration in the reaction initial stage (1 hour after reaction initiation) of the oxidation reaction of the ascorbic acid component is preferably from 1 to 10 volume %, more preferably from 2 to 10 volume %, and even more preferably from 2 to 9 volume %. Furthermore, when anaerobic bacteria are cultured, the oxygen concentration in the reaction initial stage (1 hour after reaction initiation) of the oxidation reaction of the ascorbic acid component is preferably 2 volume % or less and more preferably 1 volume % or less. The carbon dioxide concentration in the reaction initial stage (1 hour after reaction initiation) of the oxidation reaction of the ascorbic acid component is preferably 10 volume % or more, more preferably 12 volume % or more, and even more preferably 14 volume % or more.

In addition, the culturing temperature is preferably 20 to 45° C., and particularly preferably 25 to 40° C.

In the method for culturing bacteria according to the present invention, the atmosphere in the gas barrier container prior to culturing does not need to be particularly controlled, and may be, for example, air. When the gas barrier container is filled with air and the gas concentration regulator that generates carbon dioxide in a volume equivalent to that of absorbed oxygen is used to perform the culture method according to the present invention, if the carbon dioxide concentration is set to from 2 to 10 volume %, the oxygen concentration is about from 11 to 19 volume %, and if the carbon dioxide concentration is set to from 3 to 8 volume %, the oxygen concentration is about from 13 to 18 volume %. However, the oxygen concentration is not particularly limited in the culture method using the gas concentration regulator according to the present invention. Furthermore, the concentration of the aldehyde dissolved in the medium is preferably 2 mg/L or less, more preferably 1.5 mg/L or less, and even more preferably 1.0 mg/L or less, which is suitable as the culturing condition.

The bacteria used in the culture method according to the present invention are not particularly limited. The method for culturing bacteria according to the present invention can be applied to culture of any of anaerobic bacteria, microaerophilic bacteria, and aerobic bacteria. The culture medium used in the culture method according to the present invention is also not particularly limited, and the medium that is commonly used can be applied as is, so that the medium suitable for the bacteria to be cultured can be freely selected. Furthermore, the culture vessel is not particularly limited as long as the air permeability to the outside of the vessel is ensured, and any vessel having a volume, shape, material, or the like suitable for culturing can be used. A culture vessel having a lid portion is preferably used, but at this time as well, the air permeability to the outside of the vessel needs to be ensured.

The gas barrier sealed container used in the method for culturing bacteria prevents gas from flowing into/out of the container, and maintains the oxygen and carbon dioxide concentrations formed by the fed gas concentration regulator for a long period of time. A container made of glass, metal, plastic such as polycarbonate, or the like is often used, but it is also possible to use a gas-barrier film and a laminate thereof.

According to the culture method of the present invention, microscopic observation and transport of bacteria under a suitable gas atmosphere is enabled without using a gas cylinder and a gas controller.

EXAMPLES

Hereinafter, the present embodiment will be described in detail using Examples and Comparative Examples, but the present embodiment can be modified as appropriate as long as the present embodiment achieves the effects of the present invention. Note that "parts" in Examples and Comparative Examples refer to parts by mass when not specifically stated.

The activated carbon used in Examples and Comparative Examples is shown in Table 1. The average pore diameter and total pore volume of the activated carbon were measured by the following method.
(Average Pore Diameter and Total Pore Volume of Activated Carbon)

For measuring the average pore diameter and the total pore volume of the activated carbon, approximately 0.1 g of a sample was vacuum-degassed at 130° C. as a pretreatment condition, and a nitrogen adsorption isotherm in liquid nitrogen (77 K) was measured using "BELSORP-max" available from MicrotracBel Corporation. The total pore volume and the average pore diameter were determined by a BET multi-point method using accompanying software.

TABLE 1

| Activated carbon No. | Product name | Manufacturer | Total pore volume ($cm^3/g$) | Average pore diameter (nm) |
|---|---|---|---|---|
| C1 | Taiko SGP-H | Futamura Chemical Co., Ltd. | 1.92 | 4.8 |
| C2 | SHIRASAGI A | Osaka Gas Chemicals Co., Ltd. | 0.71 | 2.7 |
| C3 | SHIRASAGI A-3 Modification | Osaka Gas Chemicals Co., Ltd. | 0.81 | 3.0 |
| C4 | FP-3 | Osaka Gas Chemicals Co., Ltd. | 0.84 | 2.0 |
| C5 | FP-9 | Osaka Gas Chemicals Co., Ltd. | 0.53 | 1.9 |

Example 1

In 100 g of an aqueous solution of sodium L-ascorbate (concentration: 45 mass %), 6 g of ferrous sulfate heptahydrate was dissolved, and after 60 g of activated carbon (C1) was impregnated with the aqueous solution, 70 g of low molecular weight polyethylene and 20 g of sodium carbonate decahydrate were added thereto and mixed to obtain a gas concentration regulator (1).

In addition, an air-permeable individual bag of 90 mm in length by 55 mm in width made of Japanese washi paper laminated with a perforated polyethylene film is filled with 5 g of the gas concentration regulator (1), and a gas concentration regulator package (1) was made.

Examples 2 to 4

Gas concentration regulators (2) to (4) and gas concentration regulator packages (2) to (4) were made in the same manner as in Example 1 except that the activated carbon (C1) was changed to activated carbons (C2) to (C4), respectively.

Comparative Example 1

A gas concentration regulator (5) and a gas concentration regulator package (5) were made in the same manner as in Example 1 except that the activated carbon (C1) was changed to activated carbon (C5).
[Evaluation]

Oxygen gas concentration and carbon dioxide gas concentration were measured using the following method for the gas concentration regulator packages (1) to (5) made in Examples and Comparative Examples. The results are shown in Table 2.
(Oxygen Gas Concentration and Carbon Dioxide Gas Concentration)

A gas concentration regulator package, two dishes for measuring aldehyde (60 mm in diameter, including 5 mL of distilled water), and 2.5 L of air were sealed in a bag (400×220 mm) of nylon film coated with polyvinylidene chloride, which was kept warm in a constant-temperature bath at 35° C., and a change over time of the in-bag gas components was measured. The changes in oxygen gas concentration and carbon dioxide gas concentration over time were measured simultaneously using an oxygen/carbon dioxide gas analyzer "CheckMate 3" (available from MOCON Europe A/S).

TABLE 2

|  |  | 1 h Average | 2 h Average | 24 h Average | 48 h Average | 72 h Average |
|---|---|---|---|---|---|---|
| Example 1 | $O_2$ concentration (%) | 15.5 | 15.2 | 13.6 | 13.0 | 12.8 |
|  | $CO_2$ concentration (%) | 4.3 | 4.7 | 6.9 | 7.8 | 8.0 |
| Example 2 | $O_2$ concentration (%) | 13.0 | 12.7 | 11.5 | 11.2 | 11.0 |
|  | $CO_2$ concentration (%) | 6.9 | 7.3 | 8.5 | 8.7 | 8.8 |
| Example 3 | $O_2$ concentration (%) | 13.3 | 13.2 | 12.1 | 11.8 | 11.7 |
|  | $CO_2$ concentration (%) | 6.7 | 6.9 | 8.1 | 8.3 | 8.4 |
| Example 4 | $O_2$ concentration (%) | 16.8 | 15.0 | 12.1 | 11.8 | 11.6 |
|  | $CO_2$ concentration (%) | 2.9 | 4.8 | 8.2 | 8.3 | 8.4 |
| Comparative Example 1 | $O_2$ concentration (%) | 19.7 | 19.0 | 11.7 | 11.4 | 11.2 |
|  | $CO_2$ concentration (%) | 0.4 | 0.9 | 8.4 | 8.6 | 8.7 |

As is clear from Table 2, in Comparative Example 1 in which the activated carbon (C5) having an average pore diameter of less than 2.0 nm was used, the carbon dioxide concentration was low after 1 to 2 hours from start of the oxidation reaction of the ascorbic acid component, and the amount of carbon dioxide generated in the reaction initial stage was small. In contrast, in Examples each of which the activated carbon having an average pore diameter of 2.0 nm or more was used, carbon dioxide generation concentration 1 hour after the start of the oxidation reaction of the ascorbic acid component was high, and it was possible to produce a gas environment with a high-concentration carbon dioxide atmosphere and a low-concentration oxygen atmosphere in a short period of time.

The invention claimed is:

1. A gas concentration regulator for use in culture of bacteria, comprising: (a) an ascorbic acid component; (b) a transition metal catalyst; (c) activated carbon; (d) an alkali metal carbonate or an alkaline earth metal hydroxide; (e) water; and a thermoplastic resin;
   wherein the activated carbon is impregnated with the ascorbic acid component and the water,
   the activated carbon is a granular activated carbon having a particle diameter of 0.1 to 2 mm;
   an average pore diameter of the activated carbon is 2.7 nm or more and 5.5 nm or less, and
   a total pore volume of the activated carbon is 0.60 cm³/g or more and
   wherein the thermoplastic resin is polyethylene, polypropylene, or a mixture thereof having a molecular weight of 10,000 or less, and
   the thermoplastic resin has a softening point of 90° to 125° C.

2. The gas concentration regulator according to claim 1, wherein the average pore diameter of the activated carbon is 2.7 nm or more and 5.0 nm or less.

3. The gas concentration regulator according to claim 1, wherein a total pore volume of the activated carbon is 0.65 cm³/g or more.

4. A method of culturing bacteria, comprising culturing bacteria in the presence of the gas concentration regulator according to claim 1.

5. A gas concentration regulator package, in which the gas concentration regulator according to claim 1 is bagged in an individual bag using an air-permeable packaging material.

* * * * *